United States Patent [19]

Franz

[11] Patent Number: 5,914,407
[45] Date of Patent: Jun. 22, 1999

[54] PREPARATION OF PIPERID-2-ONE

[75] Inventor: Lothar Franz, Mutterstadt, Germany

[73] Assignee: BASF Aktiengesellschaft, Ludwigshafen, Germany

[21] Appl. No.: 08/395,595

[22] Filed: Feb. 28, 1995

[30] Foreign Application Priority Data

Mar. 2, 1994 [DE] Germany ............................ 44 06 789

[51] Int. Cl.$^6$ ................................................ C07D 211/36
[52] U.S. Cl. .......................................................... 546/243
[58] Field of Search ............................................. 546/243

[56] References Cited

U.S. PATENT DOCUMENTS 3,775,431 11/1973 Rodewald .......................... 2610/326.5
3,975,400 8/1976 Himmele et al. .................... 260/326.5

FOREIGN PATENT DOCUMENTS 2102606 of 1972 France .

OTHER PUBLICATIONS

*Chemical Abstracts* vol. 121 No. 231278, Dell et al. (1994) "A Diastereo Selective Approach to Alpha–Allyl–Beta–Amino Acids".
Allgemeine und Praktische Chemie (1966) pp. 618–619.
Liebigs Ann. Chem. vol. 716 (1968) pp. 83–86.
Chem. Abstr., vol. 64 (1966) 8044b.
Ono et al, Ind. Eng. Chem., Prod. Res. Dev., vol. 15, Sep. 1976, pp. 180–182.

*Primary Examiner*—John Kight
*Assistant Examiner*—Raymond Covington
*Attorney, Agent, or Firm*—John H. Shurtleff

[57] ABSTRACT

A process for preparing piperid-2-one by reacting polymers of delta-valerolactone having a molecular weight of from 200 to 20,000 with ammonia under an inert atmosphere at temperatures of from 250 to 500° C. and pressures of from 30 to 500 bar in valerolactone or in an inert solvent thereby avoiding the use of any special catalyst.

12 Claims, No Drawings

PREPARATION OF PIPERID-2-ONE

The present invention relates to a process for preparing piperid-2-one by reaction of polymers of delta-valerolactone having a molecular weight of from 200 to 20,000 with ammonia at elevated temperatures and pressures, which works without a Friedel-Crafts catalyst.

A process for preparing piperid-2-one by reaction of delta-valerolactone with ammonia is known from Allgemeine und Praktische Chemie (1966), 618 to 619.

A process for the cyclization of the ammonium salt of 5-hydroxy-valeric acid is known from Liebigs Ann. Chem. 716 (1968), 83 to 86. Temperatures of over 300° C. and pressures of 100 bar are required for this reaction.

It is generally known that valerolactone is catalytically polymerized at room temperature even by small amounts of water and therefore water-containing crude products partially polymerize even before distillation.

The reaction of polymers of delta-valerolactone to give piperidone in the presence of Friedel-Crafts catalysts at from 230 to 300° C. by amination is known from Chem. Abstr., Vol. 64 (1966), 8044b. Suitable catalysts are eg. anhydrous chlorides or bromides of Fe, Al, Zn, Sn or Sb in a concentration of up to 1%.

The disadvantages of this procedure are the catalysts used, which can cause both difficulties in handling and corrosion problems.

It is an object of the present invention to avoid the abovementioned disadvantages.

We have found that this object is achieved by a novel and improved process for preparing piperid-2-one, which comprises reacting polymers of delta-valerolactone having a molecular weight of from 200 to 20,000 with ammonia at from 250 to 500° C. and from 30 to 500 bar in valerolactone or in an inert solvent in the absence of a Friedel-Crafts catalyst.

The process according to the invention can be carried out as follows:

A mixture or solution of polymers of delta-valerolactone having a molecular weight of from 200 to 20,000, preferably from 500 to 5,000, particularly preferably from 1,500 to 4,000 (determined by osmometry) and a mixing agent or solvent can be reacted batchwise or continuously, preferably continuously, under an inert gas atmosphere at from 250 to 500° C., preferably from 270 to 400° C., particularly preferably from 280 to 330° C. and from 30 to 500 bar, preferably from 50 to 400 bar, particularly preferably from 100 to 300 bar in the absence of a Friedel-Crafts catalyst (Chem. Abstr., Vol. 64 (1966), 8044b), preferably in the absence of an amination catalyst in pressure equipment such as autoclaves and tubular reactors.

Suitable inert gases under these reaction conditions are hydrogen, nitrogen and rare gas.

Suitable mixing agents or solvents are valerolactone, in particular delta-valerolactone, or solvents which are inert under the reaction conditions, such as pyridine, triethylene glycol, diethylene glycol, 1,2-dimethoxyethane and tetrahydrofuran, preferably N,N'-dimethylethylene- and N,N'-dimethylpropyleneurea, particularly preferably lactams having a tertiary nitrogen, such as N-methylpyrrolidone, N-octylpyrrolidone, 1-dodecylpyrrolidone and 1-(2-ethylhexyl)pyrrolidone.

Piperid-2-one is suitable as an intermediate for pharmaceutical and crop protection active compounds.

EXAMPLES

Example 1

600 ml of ammonia were added in an autoclave to a mixture of 198 g of the solid polymer having a molecular weight determined by osmometry of 2,310 and 99 g of valerolactone and the mixture was reacted at 330° C. for 4 h under a hydrogen pressure of 280 bar. After distillation in vacuo, 199 g (68%) of piperidone were obtained.

Example 2

400 ml of ammonia were added in an autoclave to a mixture of 236 g of the solid polymers as in Example 1 and 197 g of N-methylpyrrolidone and the mixture was reacted as before. After distillation in vacuo, 195 g (83%) of piperidone were obtained.

I claim:

1. A process for preparing piperid-2-one which comprises reacting polymers of delta-valerolactone having a molecular weight of from 200 to 20,000 with ammonia under an inert atmosphere at a pressure of from 30 to 500 bar and at a temperature of from 250 to 500° C. in valerolactone or an inert solvent or mixtures thereof as a liquid phase reaction medium.

2. A process as claimed in claim 1 wherein said polymers have a molecular weight of from 500 to 5,000.

3. A process as claimed in claim 1 wherein said polymers have a molecular weight of from 1,500 to 4,500.

4. A process as claimed in claim 1 wherein the reaction is carried out at a pressure of from 80 to 400 bar and a temperature of from 270 to 400° C.

5. A process as claimed in claim 1 wherein the reaction is carried out at a pressure of from 100 to 300 bar and a temperature of from 280 to 330° C.

6. A process as claimed in claim 1 wherein the reaction is carried out in a liquid reaction medium consisting essentially of delta-valerolactone.

7. A process as claimed in claim 1 wherein the reaction is carried out in a liquid reaction medium consisting essentially of a lactam having a tertiary nitrogen atom.

8. A process as claimed in claim 7 wherein the lactam is N-methylpyrrolidone.

9. A process as claimed in claim 1 wherein the reaction is carried out in a liquid reaction medium selected from the group consisting of delta-valerolactone, pyridine, triethylene glycol, diethylene glycol, 1,2-dimethoxyethane, tetrahydrofuran, N,N'-dimethylethyleneneurea, N,N'-dimethylpropyleneneurea, N-methylpyrrolidone, N-octylpyrrolidone, N-dodecylpyrrolidone and 1-(2-ethylhexyl)-pyrrolidone.

10. A process as claimed in claim 1 wherein the reaction is carried out under an inert gas selected from the group consisting of hydrogen, nitrogen and a rare gas.

11. A process as claimed in claim 10 wherein the reaction is carried out under a gas pressure of from 50 to 400 bar.

12. A process as claimed in claim 10 wherein the reaction is carried out under a gas pressure of from 100 to 300 bar.

* * * * *